US005950622A

United States Patent [19]

Pomerantz

[11] Patent Number: 5,950,622

[45] **Date of Patent: *Sep. 14, 1999**

[54] SCUBA DIVING BREATHING REGULATOR

[75] Inventor: Mitchell P. Pomerantz, Highland Park, Ill.

[73] Assignee: Johnson Worldwide Associates, Sturtevant, Wis.

[ * ] Notice: This patent is subject to a terminal disclaimer.

[21] Appl. No.: 08/915,794

[22] Filed: Aug. 21, 1997

Related U.S. Application Data

[63] Continuation-in-part of application No. 08/702,093, Aug. 23, 1996, Pat. No. 5,690,100.

[51] Int. Cl.[6] .......................... A61M 16/00; A62B 7/04; F16K 31/26

[52] U.S. Cl. .......................... 128/204.26; 128/205.24

[58] Field of Search .......................... 128/201.27, 205.24, 128/204.26, 201.28; 137/375, 908

[56] References Cited

U.S. PATENT DOCUMENTS

| | | | |
|---|---|---|---|
| 3,799,189 | 3/1974 | Christianson . | |
| 3,952,773 | 4/1976 | Hahn . | |
| 4,356,820 | 11/1982 | Trinkwalder . | |
| 4,784,129 | 11/1988 | Garraffa . | |
| 4,898,205 | 2/1990 | Ross . | |
| 4,922,955 | 5/1990 | Uri . | |
| 5,158,106 | 10/1992 | McIntosh . | |
| 5,265,596 | 11/1993 | Sauze . | |
| 5,413,096 | 5/1995 | Hart . | |
| 5,655,524 | 8/1997 | Atkins | 128/205.24 |
| 5,664,565 | 9/1997 | Pietrelli | 128/205.24 |
| 5,678,541 | 10/1997 | Garraffa | 128/205.24 |
| 5,778,875 | 7/1998 | Morgan et al. | 128/204.26 |
| 5,787,882 | 8/1998 | Hamilton | 128/204.26 |
| 5,803,073 | 9/1998 | Toth | 128/205.24 |

*Primary Examiner*—John G. Weiss
*Assistant Examiner*—Joseph F. Weiss, Jr.
*Attorney, Agent, or Firm*—Foley & Lardner

[57] ABSTRACT

A breathing regulator for scuba diving includes a housing having a high pressure gas inlet and a discharge outlet in conjunction with a pressure regulator valve assembly operatively connected to the inlet. The valve assembly includes a valve support, a valve movably coupled to the valve support at a first location for movement between a first high pressure gas inlet closing position and a second high pressure gas inlet opening position and a layer of material disposed adjacent to the first location to insulate the first location.

15 Claims, 5 Drawing Sheets

SCUBA DIVING BREATHING REGULATOR

RELATED APPLICATION

The present application is a continuation-in-part of U.S. Pat. application Ser. No. 08/702,093 filed on Aug. 23, 1996, U.S. Pat. No. 5,690,100.

FIELD OF THE INVENTION

The present invention relates generally to scuba diving equipment and more particularly to a breathing regulator which prevents icing of the regulator in cold water.

BACKGROUND OF THE INVENTION

Scuba diving breathing regulators are well known in the art. Typically, they constitute the second of two stages of gas pressure regulation between one or more tanks of compressed gas and the diver's respiratory system. Thus, one of the principal functions of a scuba diver's breathing regulator is to provide gas to the diver at the appropriate pressure to enable the diver to breathe normally under water. For each breathing cycle, high pressure gas flows through the valve orifice and into the breathing chamber. As this gas flows through and around the valve mechanism it rapidly expands into the breathing chamber and a pressure drop occurs. This rapid pressure drop and expanse of gas causes a cooling condition. If scuba diving in cold water, the valve mechanism and housing of the regulator can become supercooled below the freezing point of water. If moisture is present in the regulator housing, either from exhaled breath or the surrounding environment, it will condense and freeze on these supercooled parts causing an icing condition within the regulator housing. Ice can continue to build up to the point where it can block the mechanism from proper operation. The valve mechanism freezes in an open position bringing about continued cooling and freezing and thereby causing a dangerous breathing condition in addition to a rapid depletion of the diver's gas supply. As a result, there has been a need for an improved breathing regulator which overcomes the aforementioned disadvantage. More specifically, there is a need to insulate the brass tube in the gas control system to prevent icing of the metallic parts.

SUMMARY OF THE PRESENT INVENTION

The present invention is directed to improved breathing regulator for scuba diving. The regulator includes a housing having a high pressure gas inlet and a discharge outlet in conjunction with a pressure regulator valve assembly operatively connected to the inlet. The valve assembly includes a valve support, a valve movably coupled to the valve support at a first location for movement between a first high pressure gas inlet closing position and a second high pressure gas inlet opening position, and a layer of material disposed adjacent to the first location to insulate the first location.

The present invention is more specifically directed to the aforementioned regulator wherein the valve support is made of a material having a first thermal conductivity and wherein the layer of material has a second lesser thermal conductivity. The valve support is preferably made of metal, whereas the layer of material is preferably made of plastic. Alternatively, or additionally, the layer of material is preferably disposed adjacent to the first location so as to create an insulating air gap between the layer and the first location.

The present invention is also more specifically directed to aforementioned regulator wherein the valve support comprises a tube having a length and wherein the layer extends along at least a portion of length adjacent to the first location. The layer of material is preferably disposed on an outer surface of the tube. In one embodiment, the layer of material extends along the entire length of the tube. The valve itself preferably includes a poppet biased against the high pressure gas inlet to close the high pressure gas inlet and a lever pivotally coupled to the valve support at the first location and in engagement with the poppet to move the poppet to the second high pressure gas inlet opening position. The regulator preferably includes a spring coupled to the poppet for biasing the poppet in the first high pressure gas inlet closing position. The regulator also preferably includes a diaphragm operatively positioned to engage the lever to move the poppet towards the second high pressure gas inlet opening position upon a drop in pressure in the housing. In addition, the regulator preferably includes a mouthpiece extending from the housing in communication with an interior of the housing for inhalation of inlet gas and exhalation of exhaust gas. An exhaust valve is preferably located in one wall of the housing for directing exhaust gas out of the interior.

Figure 2:
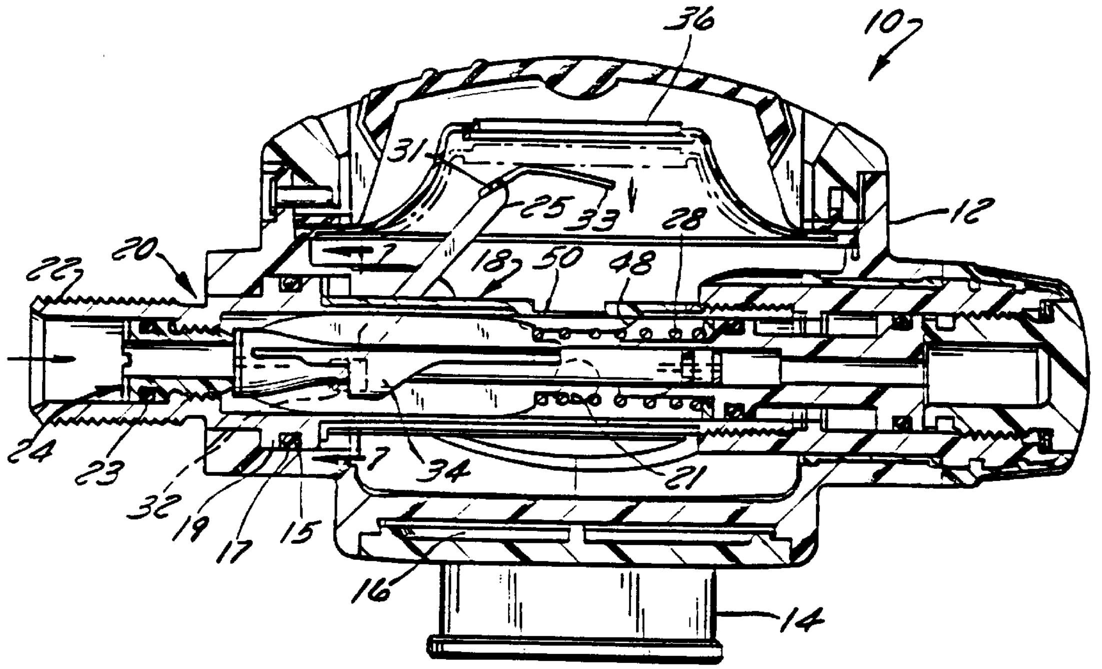
FIG. 2 is a cross sectional view taken on line 2—2 of FIG. 1 of the regulator with the pressure valve shown in the closed position.

Before explaining at least one embodiment of the invention in detail it is to be understood that the invention is not limited in its application to the details of construction and the arrangement of the components set forth in the following description or illustrated in the drawings. The invention is capable of other embodiments or being practiced or carried out in various ways. Also, it is to be understood that the phraseology and terminology employed herein is for the purpose of description and should not be regarded as limiting.

DETAILED DESCRIPTION OF THE PREFERRED EMBODIMENTS

Figure 1:
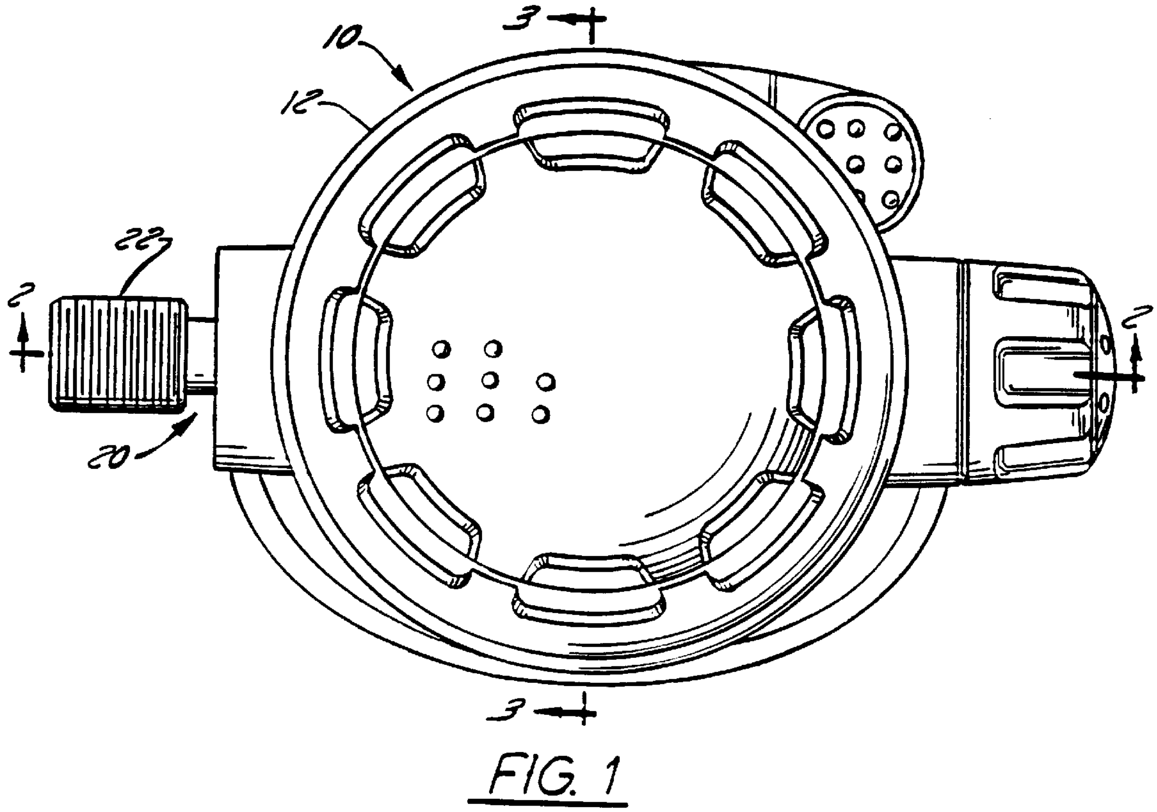
FIG. 1 is a top view of a breathing regulator according to the present invention.
Figure 3:
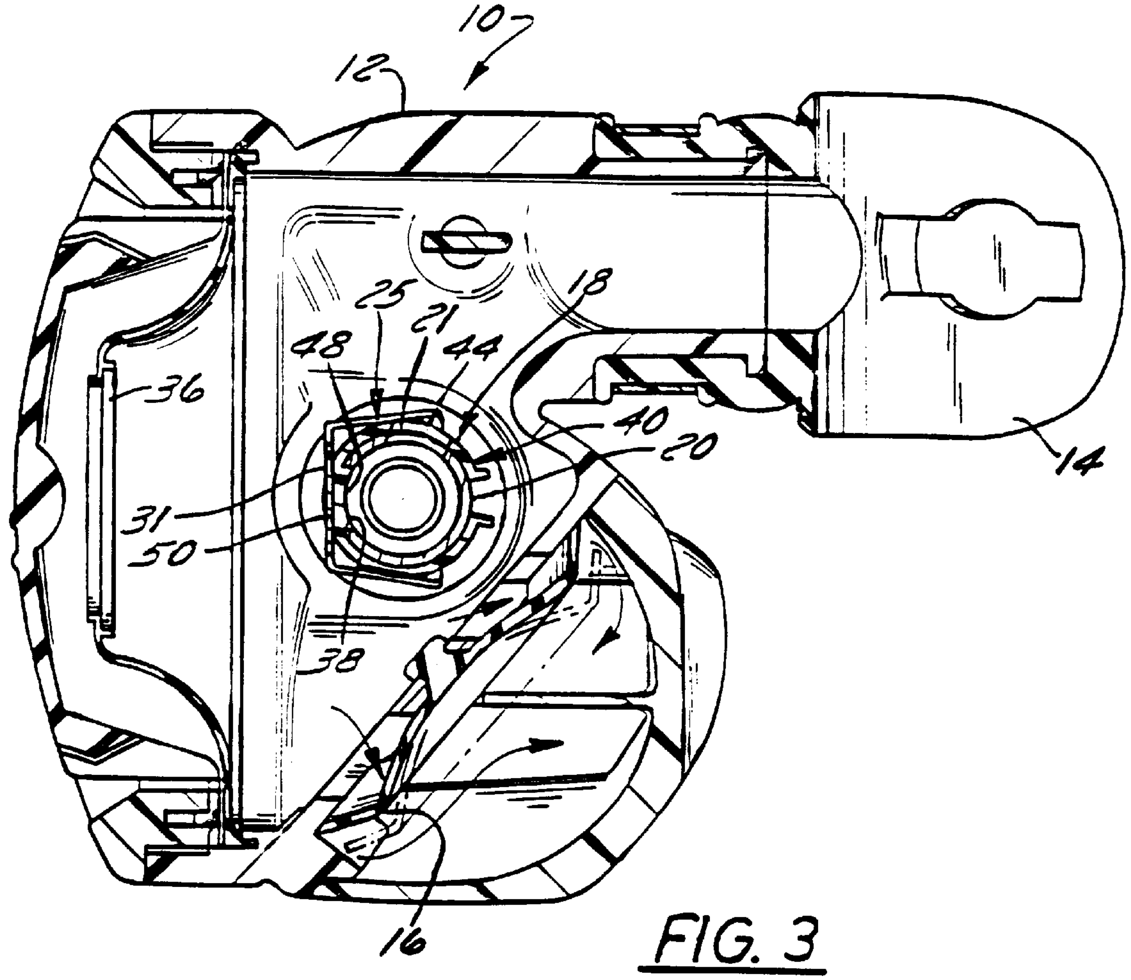
FIG. 3 is a cross sectional view taken on line 3—3 of FIG. 1 of the regulator.

Referring to FIGS. 1, 2 and 3 a typical breathing regulator 10 is shown having a housing 12, a mouthpiece 14 and an exhaust valve 16. A gas control regulator assembly 18 is mounted in the housing 12. The regulator assembly 18 includes a brass tube 20 having a threaded inlet 22 operatively connected to a high pressure gas source (not shown). The brass tube 20 is sealed in the housing by means of an O-ring 15 mounted in a groove 17 formed in flange 19. A high pressure valve orifice 24 is mounted in the inlet 22 of the brass tube 20. An outlet 21 is provided in the side of the brass tube for discharge of high pressure gas into the housing 12. The valve orifice 24 is sealed in the inlet 22 by means of an O-ring 23.

A valve poppet 26 is mounted in the brass tube 20 for movement between open and closed positions with respect to the valve orifice 24. The valve poppet is biased by a spring 28 to a closed position with respect to the valve orifice 24. The valve poppet 26 is opened by means of a lever 25 pivotally mounted on the brass tube 20 by means of a pair of inwardly projecting tabs 30 which are aligned in openings 32 in the brass tube 20 and positioned to operatively engage vanes 34 provided on the valve poppet 26. The valve poppet 26 is aligned in the brass tube by flanges 27.

Figure 6:
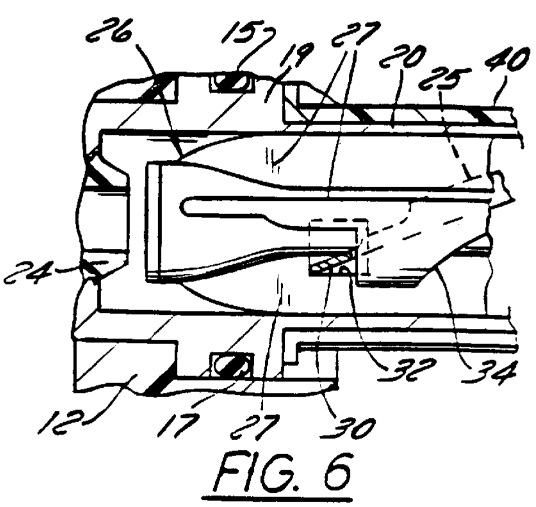
FIG. 6 is a view similar to FIG. 5 showing the lever for the pressure valve in the open position.
Figure 9:
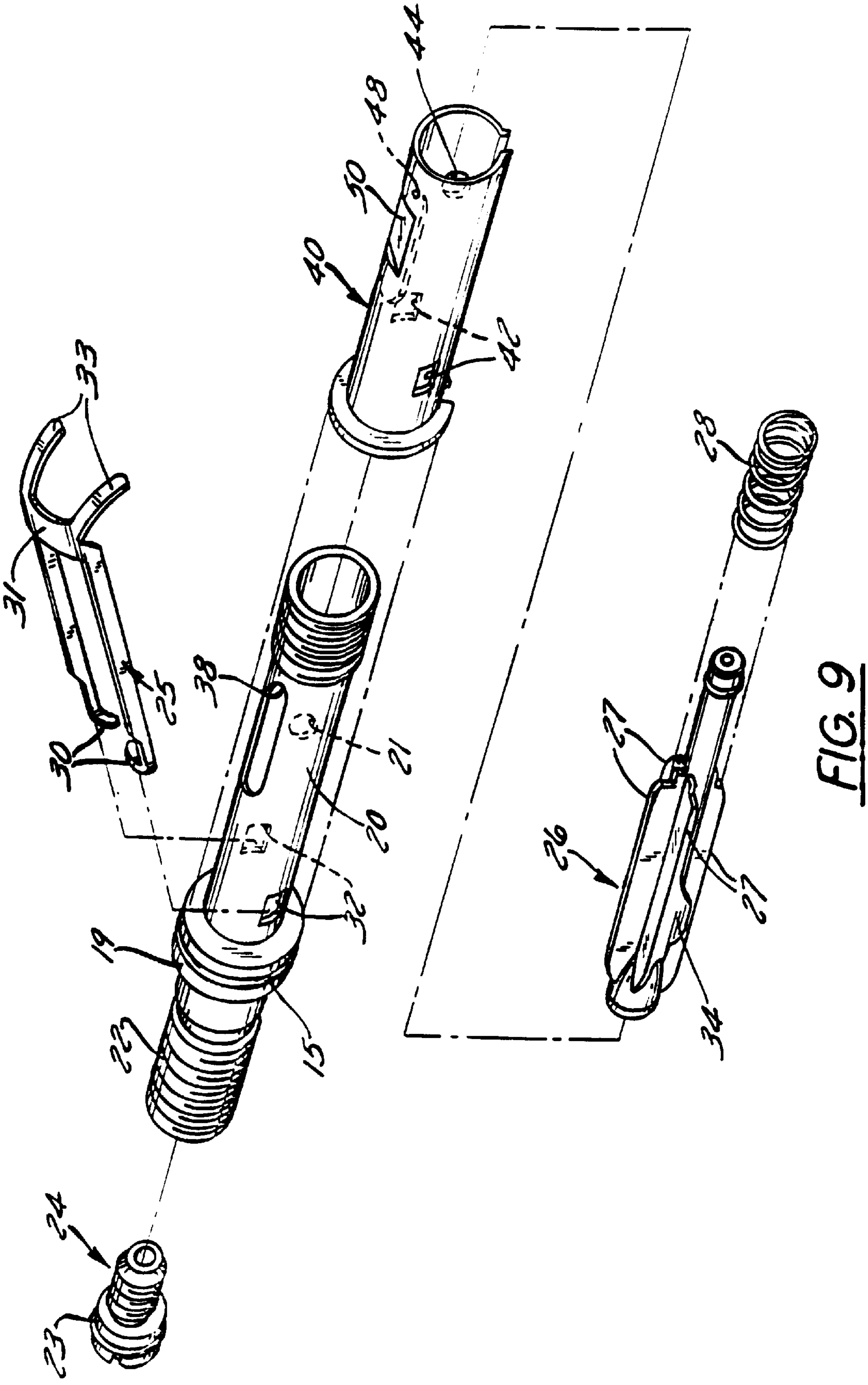
FIG. 9 is an exploded perspective view of the valve actuator assembly with the insulating sleeve aligned with the tube.

A diaphragm 36 is mounted in the top member 29 of the housing which operatively engages the top of the lever 25. The operator inhales gas through the mouthpiece 14 which collapses the diaphragm 36 into engagement with the lever 25. The lever 25 pivots into engagement with the brass tube 20 to move the valve poppet 26 away from the valve orifice 24 as shown in FIG. 6. An oval opening 38 is provided in the brass tube 20.

In accordance with the present invention, an insulating sleeve 40, formed from a plastic material such as Delrin 500, is mounted on the brass tube 20 with openings 42 in the sleeve 40 aligned with the openings 32 in the brass tube 20. The inwardly projecting tabs 30 on the lever 25 are thereby aligned with the openings 42 in the insulating sleeve 40 and the openings 32 in the brass tube 20. The tabs 30 are aligned with the vanes 34 provided on the valve poppet 26. A gas outlet 44 is provided in the sleeve 40 and aligned with the gas outlet 21 in the brass tube 20.

The insulating sleeve 40 is provided with an oval plug 48 which matingly engages the oval opening 38 to prevent any movement between the plastic tube with respect to the brass tube. A recess 50 is provided in the surface of the sleeve to accommodate the cross member 31 on the lever 25 between the tongs 33 which allows for additional travel of the lever for increased valve opening.

In operation, the diaphragm 36 collapses onto the lever 25 to pivot downward into engagement with the vane 34. The tabs 30 pivot in openings 32 and 42 to push the vane 34 on valve poppet 26 to open the valve orifice 24 to admit high pressure gas into the housing. As the pressure increases in the housing, the diaphragm 36 moves away from the tube 20, allowing the lever 25 to also pivot. The spring 28 moves the valve poppet 26 into engagement with valve orifice 24, stopping the flow of high pressure gas, as the scuba diver exhales. The exhausted gas exits through the gas outlet 16.

Figures 10, 11:
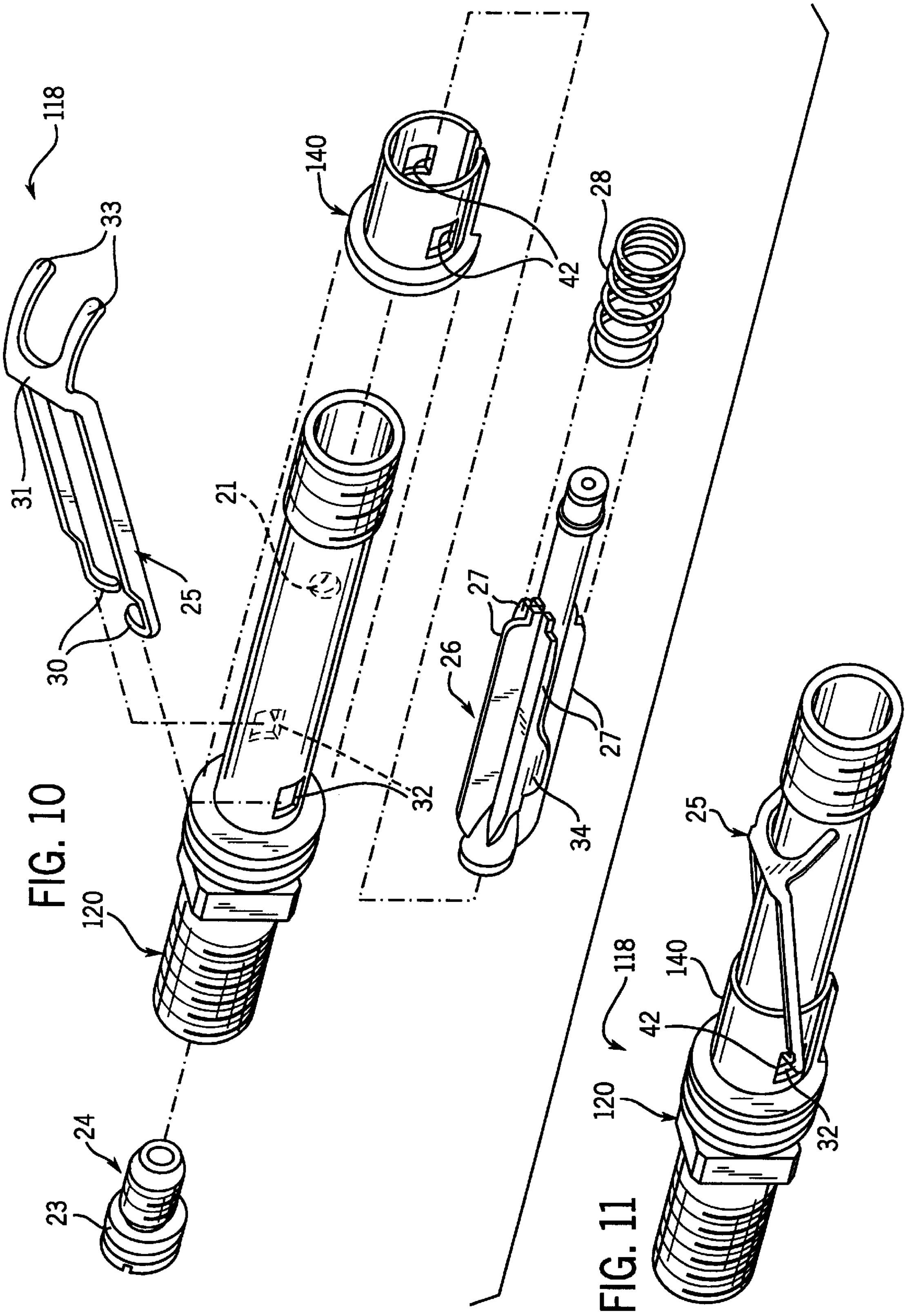
FIG. 10 is an exploded perspective view of a second embodiment of the valve actuator assembly with an insulating sleeve aligned with the tube.
FIG. 11 is a perspective view illustrating the assembled second embodiment of the valve actuator assembly.

FIGS. 10 and 11 illustrate gas controlled regulator assembly 118, an alternate embodiment of gas controlled regulator assembly 18 shown in FIGS. 1 through 9. FIG. 10 is an exploded perspective view of regulator assembly 118, while FIG. 11 is an assembled view of regulator assembly 18. Regulator assembly 118 mounts within housing 12 similar to regulator assembly 18 and operates in a similar fashion to regulator assembly 18. Regulator assembly 118 is similar to regulator assembly 18, except that regulator assembly 118 includes tube 120 and insulating sleeve 140 in lieu of tube 20 and insulting sleeve 40. For ease of illustration, those elements of regulator assembly 118 which correspond to similar elements of regulator assembly 18 are numbered similarly.

Figure 4:
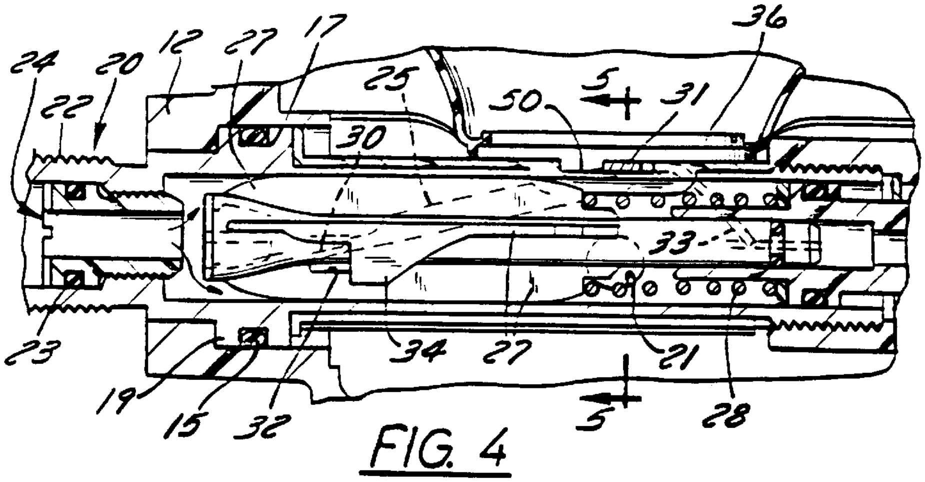
FIG. 4 is a view similar to FIG. 2 showing the pressure valve in the open position.
Figure 7:
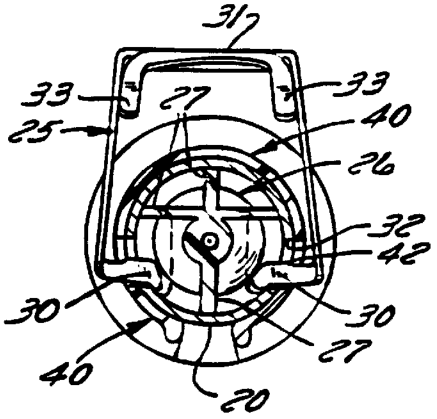
FIG. 7 is a cross sectional view taken on line 2—2 of FIG. 2 showing the lever in the valve closed position.
Figure 5:
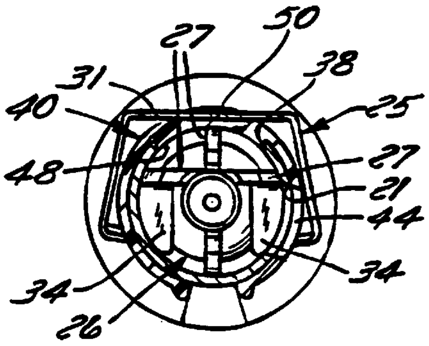
FIG. 5 is a cross sectional view taken on line 5—5 of FIG. 4 showing the lever in the open position.
Figure 8:
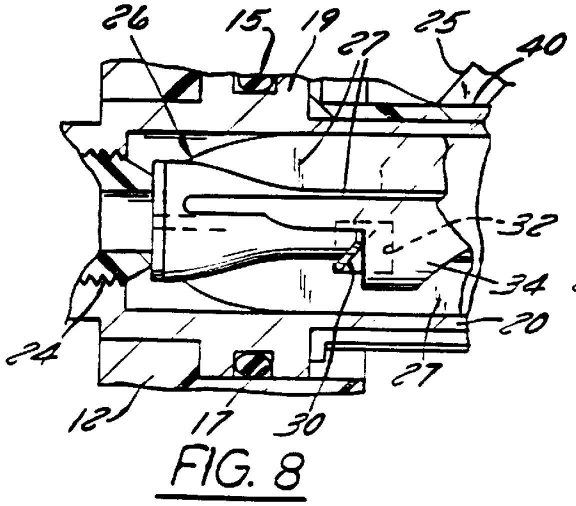
FIG. 8 is an enlarged view similar to FIG. 7 showing the pressure valve in the closed position.

As best shown by FIG. 10, tube 120 is a generally elongate support member configured for receiving and movably supporting valve poppet 26 for movement between a first high pressured gas inlet closing position in which valve poppet 26 seals valve orifice 24 (shown in FIG. 2) and a second high pressure gas inlet opening position in which valve poppet 26 opens valve orifice 24 (shown in FIG. 4). Valve poppet 26 is biased by spring 28 to the closed position with respect to valve orifice 24. As discussed above, valve poppet 26 is actuated between the first high pressure gas inlet closing position and the second high pressure gas inlet opening position by means of a lever 25 pivotally coupled to tube 120 at openings 32 and in operative engagement with vanes 34 of valve poppet 26. Lever 25, valve poppet 26, and spring 28 act as a valve for selectively opening and closing valve orifice 24 to control the admittance of high pressure gas into housing 12.

Insulating sleeve 140 is similar to insulating sleeve 40, except that insulating sleeve 140 is shortened so as to extend along only a portion of the length of tube 120. Similar to sleeve 40, sleeve 140 provides a layer of material is disposed adjacent to the location at which lever 25 is movably coupled to tube 120. In the particular embodiment illustrated in FIGS. 10 and 11, sleeve 140 provides a layer of material that is disposed on the outer surface of tube 120 adjacent to and preferably about opening 32. As a result, sleeve 140 impedes or prevents icing about opening 32 and about tabs 30 of lever 25 to insure proper operation of the valve mechanism provided by lever 25, valve poppet 26, and spring 28. In addition to insulating tube 120, sleeve 140 spaces a portion of tube 120 not covered by sleeve 140 from the interior surface of housing 12 to provide additional clearance for ice build-up.

In the preferred embodiment illustrated in FIGS. 10 and 11, tube 120 is preferably made from a metal, i.e., brass, having a first thermal conductivity, while sleeve 140 is made of a plastic material, preferably acetal 500, having a second lesser thermal conductivity. In addition, sleeve 140 may alternatively consist of two or more layers of materials, i.e., plastic, foam, metals, and the like, to provide for increased thermal resistance. Sleeve 140 is loosely positioned about tube 120 to create an air gap between tube 120 and sleeve 140. This air gap further insulates tube 120. Sleeve 140 is loosely held in place along tube 120 adjacent to openings 32 by tabs 30, which extend through both openings 42 and openings 32.

Although less desirable, sleeve 140 may alternatively be press-fit or bonded about tube 120 or may be co-molded with tube 120. Furthermore, sleeve 140 may be made of the same material as tube 120 so long as an air gap is created between sleeve 140 and tube 120 for insulating tube 120. In addition, sleeve 140 may alternately be formed on an inner circumferential surface of tube 120 adjacent to openings 32 and may alternatively extend substantially along the entire length of tube 120 similar to sleeve 40. As can be appreciated, both tube 120 and sleeve 140 may be made from a variety of alternative materials such that tube 120 securely supports the valve mechanism while sleeve 140 insulates at least the location at which the valve mechanism is movably coupled to tube 120.

Thus, it should be apparent that there has been provided in accordance with the present invention a scuba diving breathing regulator that fully satisfies the objectives and advantages set forth above. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A breathing regulator for scuba diving, the regulator comprising:

a housing having a high pressure gas inlet and a discharge outlet;

a pressure regulator valve assembly operatively connected to the inlet, the assembly including:

a valve support including a tube having a length;

a valve movably coupled to the valve support at a first location for movement between a first high pressure gas inlet closing position and a second high pressure gas inlet opening position; and a layer of material extending along a portion of the length of the tube and disposed adjacent to the first location.

2. The regulator of claim 1 wherein the layer of material is disposed adjacent to the first location so as to create an insulating air gap between the layer and the first location.

3. The regulator of claim 1 wherein the valve support is made of a material having a first thermal conductivity and wherein the layer of material has a second lesser thermal conductivity.

4. The regulator of claim 3 wherein the valve support is made of a metal and wherein the layer of material is plastic.

5. The regulator of claim 4 wherein the valve support is made of brass.

6. The regulator of claim 1 wherein the valve support comprises a tube.

7. The regulator of claim 1 wherein the valve support comprises a tube having a length and wherein the layer of material substantially extends along the entire length of the tube.

8. The regulator of claim 1 wherein the valve includes:

a poppet biased against the high pressure gas inlet to close the high pressure gas inlet; and a lever pivotally coupled to the valve support at the first location and in engagement with the poppet to move the poppet to the second high pressure gas inlet opening position.

9. The regulator of claim 8 including a spring coupled to the poppet for biasing the poppet in the first high pressure gas inlet closing position.

10. The regulator of claim 8 including a diaphragm operatively positioned to engage the lever to move the poppet towards the second high pressure gas inlet opening position upon a drop in pressure in the housing.

11. The regulator of claim 8, wherein the layer of material includes a surface against which the lever bears.

12. The regulator of claim 1 including:

a mouthpiece extending from the housing in communication with an interior of the housing for inhalation of inlet gas and exhalation of exhaust gas; and an exhaust valve located in one wall of the housing for directing exhaust gas out of the interior.

13. The regulator of claim 1 wherein the valve support includes a tube and wherein the layer of material is disposed on an outer surface of the tube.

14. The regulator of claim 13 wherein the layer of insulating material is slid about the tube.

15. A breathing regulator for scuba diving, the regulator comprising:

a housing having a high pressure gas inlet and a discharge outlet;

a pressure regulator valve assembly operatively connected to the inlet, the assembly including: a tube of the first material operatively connected to the gas inlet;

a valve poppet mounted in the tube to control the flow of high pressure gas through the tube;

a spring mounted in the tube to bias the valve poppet to a closed position;

a lever pivotally coupled to the tube at a first location to open the valve poppet;

a diaphragm operatively positioned to engage the lever to open the valve poppet on a drop in pressure in the housing; and a layer of a second material blanketed at least partially about the tube adjacent the first location to insulate the first location.

* * * * *